United States Patent [19]

Holtkamp, Sr.

[11] Patent Number: Plant 6,107

[45] Date of Patent: Feb. 16, 1988

[54] AFRICAN VIOLET PLANT NAMED MEG

[75] Inventor: Reinhold Holtkamp, Sr., Isselburg, Fed. Rep. of Germany

[73] Assignee: Gessellschaftsvertrag uber die Erfindergemeinschaft "OPTIMARA", Fed. Rep. of Germany

[21] Appl. No.: 823,476

[22] Filed: Jan. 28, 1986

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

An African violet plant named Meg having semi-double, two-tone pink flowers; girl-type leaves; strong upright stems; early and profuse flowering; compact flower head positioned above the leaves; and long-lasting and non-dropping flowers.

1 Drawing Figure

The present invention comprises a new and distinct cultivar of African violet plant, botanically known as *Saintpaulia ionantha*, and hereinafter referred to by the cultivar name Meg.

The new cultivar was originated from a cross made in a controlled breeding program in Isselburg, West Germany. The female, or seed parent was a cultivar designated 79 blue girl type. The male, or pollen parent was a cultivar designated 89 blue white frilled. The new cultivar was given the breeding number G21/VII.

Meg was discovered and selected by me as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and retained through successive generations of asexual reproduction.

Meg has not been observed under all possible environmental conditions. The phenotype may vary significantly with variations in environment such as temperature, light intensity and day length. The following observations, measurements and values describe the new cultivar as grown in Isselburg, West Germany and Nashville, Tenn. under greenhouse conditions which closely approximate those generally used in commercial practice.

The following traits have been repeatedly observed and are determined to be basic characteristics of Meg, which in combination distinguish this African violet as a new and distinct cultivar:

1. Strong, upright flower stems curving toward the center.
2. Meg is a semi-double, with a beautiful light pink flower color that intensifies toward the center.
3. Very attractive girl-type leaves that are strongly serrated with bright green centers and indented.
4. Profuse and early flowering, with compact flower head.
5. Each plant carries up to 6 and more upright flower stems, each of which carries 6 and more flowers.
6. The mature flowers dry off on the stem, preventing botrytis.
7. Plant is saleable 8 to 9 weeks after potting.
8. Medium to dark green velvety leaves, slightly hairy.

9. Long-lasting, non-dropping flowers.
10. Seed capsules pushes slightly through.

The accompanying photographic drawing shows a typical specimen plant of the new cultivar grown in a 4" pot. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 1:30 p.m. in Nashville, Tenn.

Botanical classification: *Saintpaulia ionantha*, Ramat., cv. Meg.

Parentage:

*Male parent.*—89 blue white frilled.

*Female parent.*—79 blue girl-type.

PROPAGATION

The new cultivar holds its distinguishing characteristics through successive propagations by leaf cuttings.

PLANT

From 8 cm. to 10 cm. tall when grown in pots, and approximately 20–22 cm. in diameter when fully grown.

Leaves:

*Shape.*—Generally round, girl-type, heavy indentations, serrated.

*Diameter.*—55–65 mm.

*Texture.*—Velvety, very shiny, slightly hairy.

*Ribs and veins.*—Well pronounced on under side, bright and shiny green.

*Color (upper side).*—147A.

*Color (under side).*—148D.

*Petioles.*—Strong and upright, hairy; light green with a touch of brown.

Flowers:

*Buds.*—Size: 4–5 mm. just before opening. Shape: Ball shaped.

*Sepals.*—Shape: Spear-shaped. Color: Light green.

*Calyx.*—Basifixed.

*Peduncle.*—Character: Strong, upright, hairy. Color: Brownish-green.

Individual flowers:

*Size.*—30–35 mm.

*Shape.*—Semi-double violet shape, usually with 9–12 petals, resembling a small rose.

*Color* (*upper side*).—69A, with more intense pink in center, producing a two-tone appearance.

*Color* (*underside*).—69B-C.

*Borne.*—Each flower stem carries 8–12 flowers on strong, upright peduncles, with the stems curving toward the center.

Flowering habit: Flowers 8–9 weeks after potting small plantlet; profuse flowering produces a compact flower head above the leaves; flowers are long lasting and non-dropping.

Reproductive organs:

*Stamens.*—Two.

*Anthers.*—Two, with four anther cells.

*Filaments.*—Medium pink, 3 mm.

*Styles.*—7 mm., medium pink with a light green base.

Roots: Normally developed, white when young, turning slightly brownish when older.

Disease resistance: Good.

General Observations

Meg has a very attractive appearance due to its medium to dark green leaves with bright green centers, with the leaves being below and surrounding a compact flower head comprised of semi-double, two-tone pink flowers. The flowers are carried on strong upright flower stems which curve toward the center so as to form the tight flower head. The flowers are long lasting and non-dropping.

I claim:

1. A new and distinct cultivar of African violet named Meg, as illustrated and described, and particularly characterized by its semi-double, two-tone pink flowers; girl-type leaves; strong upright stems; early and profuse flowering; a compact flower head positioned above the leaves; and by its long-lasting and non-dropping flowers.

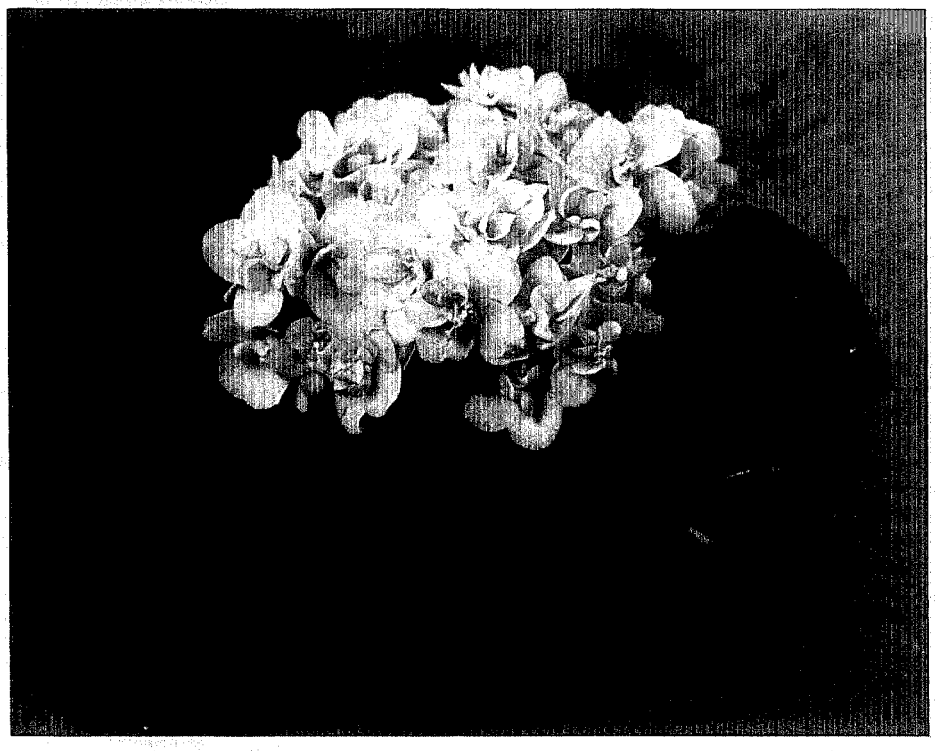

* * * * *